United States Patent [19]

Humphreys et al.

[11] Patent Number: 5,069,812

[45] Date of Patent: Dec. 3, 1991

[54] BLEACH/BUILDER PRECURSORS

[75] Inventors: Robert W. R. Humphreys, Oradell; Bijan Harirchian, South Orange, both of N.J.; Frans L. M. Smeets, Julianalaan, Netherlands

[73] Assignee: Lever Brothers Company, New York, N.Y.

[21] Appl. No.: 624,811

[22] Filed: Dec. 10, 1990

[51] Int. Cl.$^5$ .................. C09K 13/00; C11D 7/54; C07D 211/00
[52] U.S. Cl. .................. 252/186.44; 252/186.1; 252/186.42; 252/135; 252/541; 252/542; 252/174.11; 252/186.44; 546/19; 546/16; 546/20; 546/242; 546/244; 546/245; 546/224; 546/225; 546/186; 546/187; 546/188; 546/189; 546/190; 546/191
[58] Field of Search .................. 546/19, 16, 20, 242, 546/244, 245, 217, 218, 221, 222, 223, 224, 225, 186, 187, 188, 189, 190, 191; 252/186.1, 186.42, 186.44, 135, 541, 542, 174.11

[56] References Cited

U.S. PATENT DOCUMENTS

| | | |
|---|---|---|
| 2,955,905 | 10/1960 | Davies et al. |
| 3,759,833 | 9/1973 | Bannerman et al. |
| 3,966,649 | 6/1976 | Cheng |
| 4,751,015 | 6/1988 | Humphreys et al. |
| 4,818,426 | 4/1989 | Humphreys et al. |
| 4,927,559 | 5/1990 | Schwarz et al. |
| 4,931,563 | 6/1990 | Madison et al. |

OTHER PUBLICATIONS

Kurt Hermann, 1977 Abstract "Total Synthesis of Betalaines".
Organic Synthesis Coll., vol. 2, 1943, John Wiley & Sons, pp. 126-128.

*Primary Examiner*—Paul Lieberman
*Assistant Examiner*—Kevin D. McCarthy
*Attorney, Agent, or Firm*—James J. Farrell

[57] ABSTRACT

A novel multifunctional bleach/builder precursor molecule is disclosed which is useful in various detergent compositions.

6 Claims, No Drawings

BLEACH/BUILDER PRECURSORS

FIELD OF THE INVENTION

The present invention relates to novel multifunctional molecules. These novel materials are effective as both bleach precursors and builders or chelating agents and are, thus, useful in detergent compositions.

BACKGROUND OF THE INVENTION

Builders are desirable ingredients in powdered detergent formulations. Builders optimize the effectiveness of surfactants by several routes, one of which is by sequestering calcium, magnesium and other 'hardness' ions present in the wash water that adversely affect detergency.

The manner in which detergent builders improve the cleaning powers of detergent compositions is related to a combination of factors such as emulsification of soil particles, solubilization of water insoluble materials, promotion of soil suspension in the wash water so as to retard soil redeposition, sequestration of metallic ions, and the like.

Phosphates such as tripolyphosphates and pyrophosphates have been widely used as builders due to their excellent ability to sequester 'hardness' ions. However, the effect of phosphates upon the eutrophication of lakes and streams has been questioned and their use in detergent compositions has been subject to government scrutiny and regulation. Alternatives for phosphates are also widely used by detergent formulators as builders in detergent formulations. Compositions and materials change frequently as formulators attempt to improve cleaning performance while offering greater convenience in handling at lower material cost. The industry has made substantial efforts to find suitable substitutes for phosphates, however, all have one or more drawbacks that offset their value in the formulations.

In addition to builders, detergent formulations have also employed bleaches to improve soil and stain removal on clothes.

It is well known that active oxygen-releasing compounds are effective bleaching agents. These compounds are frequently incorporated into detergent compositions for stain and soil removal. Unlike the traditional sodium hypochlorite bleaches, oxygen-releasing compounds are less aggressive and thus more compatible with detergent compositions. They have, however, an important limitation; the activity of these compounds is extremely temperature dependent. Thus, oxygen-releasing bleaches are essentially only practical when the bleaching solution is heated above 60° C. At a temperature of just 60° C., extremely high amounts of the active oxygen-releasing compounds must be added to the system to achieve any bleach effect. Although this would indicate the desirability of high temperature operation, high temperatures are both economically and practically disadvantageous.

At bleach solution temperatures below 60° C., the active oxygen-releasing compounds are rendered much less effective regardless of their level in the system. With respect to bleaching of laundry in automatic household washing machines, it must be noted that these machines are normally operated at wash-water temperatures below 60° C. Consequently, a need has developed for substances which promote release of active oxygen at temperatures below 60° C. These substances are generally referred to in the art as bleach precursors, although they have also been called promoters and activators. Normally, bleach precursors are used in conjunction with persalts capable of releasing hydrogen peroxide in aqueous solution, perborate being the most widely used persalt.

Typically, the precursor is a reactive compound such as a carboxylic acid ester that in alkaline detergent solution containing a source of hydrogen peroxide, e.g. a persalt, will generate the corresponding peroxy acid. The reaction involves nucleophilic substitution onto the precursor by hydroperoxy anions (HOO$^-$) and is facilitated by precursors having good leaving groups. Often the reaction is referred to as a perhydrolysis.

There are many patents which deal with the area of bleach precursor chemistry and many of these are fully set forth in U.S. Pat. No. 4,818,426, the disclosure of which is incorporated by reference herein.

While the bleach precursors mentioned above are effective to accomplish their designed result, they still require a leaving group to activate the carbonyl carbon so as to produce the appropriate bleaching species in solution. Prior to this invention, the leaving group has not provided a significant additional washing benefit.

It has now been discovered that the leaving group can also be designed to provide a non-phosphate builder function and by judicious selection of the molecule, the leaving group can be made biodegradable and with good calcium binding ability.

1,4-Dihydro-4-oxo-2,6-pyridine dicarboxylic acid (chelidamic acid) is a well known, effective builder. In addition, we have discovered that the chelidamic acid moiety is biodegradable. The addition of chelidamic acid disodium salt to a number of acid halides which themselves contain bleach precursor molecules to generate a series of new classes of molecules is disclosed herein. These new molecules incorporate the chelidamic acid moiety as the leaving group. These new products thus provide effective metal chelation and stain bleaching simultaneously when formulated with peroxygen compounds such as sodium perborate and sodium percarbonate.

Accordingly, it is an object of the current invention to provide a multifunctional molecule which provides both good bleaching and good building.

Another object is to provide a multifunctional molecule which is both a bleach and builder precursor.

Yet another object is to provide detergent compositions employing these multifunctional molecules.

SUMMARY OF THE INVENTION

This invention broadly includes novel multifunctional compounds which are combined bleach and builder precursors. These molecules, in an appropriate environment, for example, any alkaline environment with, for example, perborates or percarbonates will undergo perhydrolysis with hydroperoxy anions and release peroxygen fragments (percarbonic acid, peroxycarboxylic acid or percarbonates or peroxycarboxylates depending on the pH) along with a metal chelating molecule.

The novel multifunctional molecules have the following general formula:

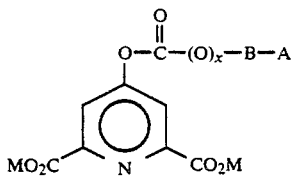

where x may be 0 or 1 and, thus, the designated oxygen molecule may be present or absent;

where M is alkali metal or hydrogen;

where B is $(CH_2)_y$ and y is 2–8 or where B is aryl, substituted aryl, such as phenyl or substituted phenyl or heterocyclic such as pyridine;

where A is R and

R may be about $C_{1-14}$ alkyl, aryl, substituted alkyl or substituted aryl, for example, phenyl or substituted phenyl, or alkyl, and the like or where A is

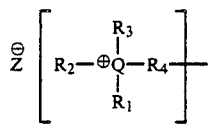

$R_1$, $R_2$ and $R_3$ are each a radical selected from the group consisting of alkyl, alkenyl, alkayl, cycloalkyl, cycloalkenyl, alkaryl, aryl, phenyl, hydroxyalkyl, polyoxyalkylene, and $R_4(O)_mC(O)_nR_1$;

or two or more of $R_1$, $R_2$ and $R_3$ together form an alkyl substituted or unsubstituted nitrogen-containing heterocyclic ring system;

or at least one of $R_1$, $R_2$ and $R_3$ is attached to $R_4$ to form an alkyl substituted or unsubstituted nitrogen-containing heterocyclic ring system; and $R_4$ is selected from a bridging group consisting of alkylene, cycloalkylene, alkylenephenylene, phenylene, arylene, and polyalkoxylene, and wherein the bridging group can be unsubstituted or substituted with $C_1$–$C_{20}$ atoms selected from alkyl, alkenyl, benzyl, phenyl and aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorus;

m and n are the same or different and either 0 or 1 or where A and B together are 2,4 pyridine dicarboxylic acid sodium salt.

Of particular interest are molecules having the following formulas:

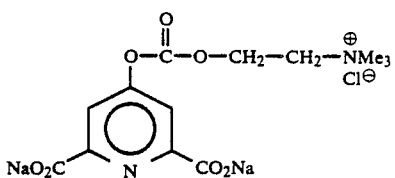

4-cholylcarbonate-2,6-pyridinedicarboxylic acid disodium salt and

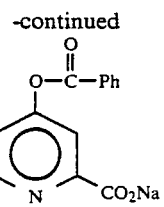

disodium 4-benzoyloxy-2,6-pyridinedicarboxylate.

The following compounds are illustrative of precursors within the present invention. It is also to be understood that upon perhydrolysis elminination of the leaving group, as defined above, there remains an organic peroxygen acid derivative of the structures outlined below.

Disodium 2-(N,N,N-Trimethylammonio)ethyl 4-(2,6-dicarboxypyridyl) carbonate chloride.

Disodium 2-(N-benzyl-N,N-dimethylammonio)ethyl 4-(2,6-dicarboxypyridyl) carbonate chloride.

Disodium 2-(N,N-ditallow-N-methylammonio)ethyl 4-(2,6-dicarboxypyridyl) carbonate chloride.

Disodium 2-(N-benzyl-N,N-diethylammonio)ethyl 4-(2,6-dicarboxypyridyl) carbonate chloride.

Disodium 2-(N-butyl-N,N-dimethylammonio)ethyl 4-(2,6-dicarboxypyridyl) carbonate bromide.

Disodium 1,1-dimethylpiperidinium-4-(2,6-dicarboxypyridyl) carbonate chloride.

Disodium 1,1-dimethylpiperidinium-3-(2,6-dicarboxypyridyl) carbonate chloride.

Disodium 4-acetyloxy-2,6-pyridinedicarboxylate.

Disodium 4-benzoyloxy-2,6-pyridinedicarboxylate.

Disodium 4-(4-methylbenzoyloxy)4-2,6-pyridine dicarboxylate.

Disodium 4-(4-methoxybenzoyloxy)4-2,6-pyridine dicarboxylate.

Disodium 4-(4-dimethylaminobenzoyloxy)4-2,6-pyridine dicarboxylate.

Disodium 4-(4-N,N-dimethylacetamidobenzoyloxy)4-2,6-pyridine dicarboxylate.

Disodium 4-(1,1-dimethylpiperidiniumoxy)4-2,6-pyridine dicarboxylate.

PREPARATION

Phenols in general will readily react with acid halides under aqueous basic conditions. For example, sodium 4-sulfophenol reacts with cholyl chloroformate and sodium 4-sulfobenzoyl chloride in the presence of NaOH/H$_2$O to yeild cholyl 4-sulfophenyl carbonate (CSPC) and 4-benzoyloxy-4-benzenesulfonic acid sodium salt, respectively, according to the following scheme 1:

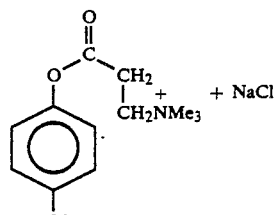

(CSPC)

TO

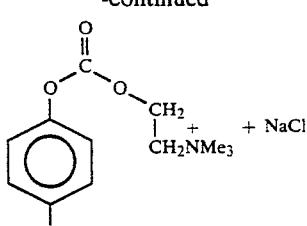

(CSPC)

Both of these molecules CSPC and P-15 are bleach precursors and are fully described in U.S. Pat. No. 4,818,426 mentioned above. These bleach precursors provide outstanding stain bleaching even at low temperatures. The leaving group phenolsulfonate, however, has no substantial activity.

Chelidamic acid also reacts with acid halides such as benzoyl chloride, 3-chloromethyl benzoyl chloride and choline chloroformate in the presence of NaOH/H$_2$O to afford disodium 4-benzoyloxy-2,6-pyridinedicarboxylic acid (BPD), disodium 4-(3-chloromethyl)benzoyloxy-2,6-pyridinedicarboxylic acid (CBPD) and disodium 4-cholinecarbonate-2,6-pyridinedicarboxylic acid (CCPD), respectively. Products thus prepared incorporated the chelidamic acid as a leaving group rather than the phenolsulfonate. Chelidamic acid, as mentioned above, provides biodegradable calcium binding activity. These products thus demonstrate stain bleaching and calcium binding simultaneously as a unique package. Synthesis of these materials is outlined in scheme 2:

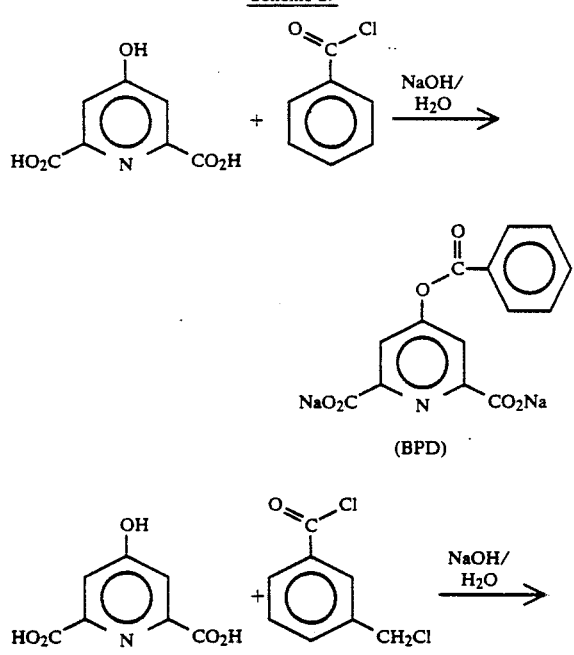

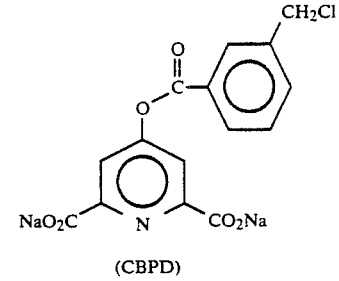

The foregoing precursors may be incorporated into detergent bleach compositions which require as an essential component a peroxygen bleaching compound capable of yielding hydrogen peroxide in an aqueous solution.

The precursors of this invention may also be used in combination with other precursors. Optional precursors which may be utilized include:

(a) N-diacylated and N,N'-polyacylated amines, such as N,N,N',N'-tetraacetyl methylene diamine and N,N,N',N'-tetraacetyl ethylene diamine, N,N-diacetylaniline, N,N-diacetyl-p-toluidine; 1,3-diacylated hydantoins such as, for example, 1,3-diacetyl-5,5-dimethylhydantoin and 1,3-dipropionyl hydantoin; acetoxy-(N,N,N')-polyacylmalonamide, for example acetoxy-(N,N')-diacetyl malonamide;

(b) N-alkyl-N-sulphonylcarbonamides, for example the compounds N-methyl-N-mesyl acetamide, N-methyl-N-mesylbenzamide, N-methyl-N-mesyl-p-nitrobenzamide, and N-methyl-N-mesyl-p-methoxybenzamide;

(c) N-acylated cyclic hydrazides, acylated triazones or urazoles, for example monacetylmaleic acid hydrazide;

(d) O,N,N-trisubstituted hydroxylamines, such as O-benzoyl-N,N-succinylhydroxylamine, O-acetyl-N,N-succinylhydroxylamine, O-p-methoxybenzoyl-N,N-succinylhydroxylamine, O-p-nitrobenzoyl-N,N-succinylhydroxylamine and O,N,N-triacetylhydroxylamine;

(e) N,N'-diacylsulphurylamides, for example, N,N'-dimethyl-N,N-diacetylsulphurylamide and N,N'-diethyl-N,N'-dipropionylsulphurylamide;

(f) Triacylcyanurates, for example triacetyl cyanurate and tribenzoyl cyanurate;

(g) Carboxylic acid anhydrides, such as benzoic anhydride, m-chloro benzoic anhydride, phthalic anhydride, 4-chlorophthalic anhydride;

(h) Esters, for example glycose pentaacetate, xylose tetraacetate, sodium acetyloxybenzenesulfonate, sodium nanoyloxybenzenesulfonate and sodium benzoyloxybenzenesulfonate;

(i) 1,3-Diacyl-4,5-diacyloxy imidazolidine, for example
1,3-diformyl-4,5-diacetoxy imidazolidine,
1,3-diacetyl-4,5-diacetoxy imidazolidine,
1,3-diacetyl-4,5-dipropionyloxy imidazoline;

(j) Tetraacetylglycoluril and tetrapropionylglycoluril;

(k) Diacylated 2,5-diketopiperazine, such as
1,4-diacetyl-2,5-diketopiperazine,
1,4-dipropionyl-2,5-diketopiperazine and
1,4-dipropionyl-3,6-dimethyl-2,5-diketopiperazine;

(l) Acylation products of propylenediurea or 2,2-dimethylpropylenediurea (2,4,6,8-tetraaza-bicyclo-(3,3,1)-nonane-3,7-dione or its 9,9-dimethyl derivative), especially the tetraacetyl- or the tetrapropionylpropylenediurea or their dimethyl derivatives;

(m) Carbonic acid esters, for example the sodium salts of p-(ethoxycarbonyloxy) benzoic acid and p-(propoxycarbonyloxy) benzenesulphonic acid;

(n) Acyloxy-(N,N')-polyacylmalonamides, such as alpha-acetoxy(N,N')-diacetylmalonamide; and (o) Quarternary ammonium substituted peroxycarbonic or carboxylic acid esters such as 2-(N,N,N-trimethylammonium)ethyl 4-sulphophenyl carbonate.

The precursors mentioned under (a), (h) and (j) are of special interest, particularly N,N,N',N'-tetraacetyl-ethylene-diamine (TAED), tetraacetyl-glycoluril (TAGU), glucose pentaacetate, xylose tetraacetate, sodium acetyloxybenzenesulfonate (SABS) and sodium nonanoyloxybenzenesulfonate (SNOBS).

Hydrogen peroxide sources are well known in the art. They include the alkali metal peroxides, organic peroxide bleaching compounds such as urea peroxide, and inorganic persalt bleaching compounds, such as the alkali metal perborates, percarbonates, perphosphates and persulfates. Mixtures of two or more such compounds may also be suitable. Particularly preferred are sodium perborate tetrahydrate, sodium percarbonate, and, especially, sodium perborate monohydrate. Sodium perborate monohydrate is preferred because it has excellent storage stability and dissolves very quickly in aqueous bleaching solutions. Rapid dissolution is believed to permit formation of higher levels of percarboxylic acid which enhances surface bleaching performance.

A detergent formulation containing a bleach system consisting of an active oxygen releasing material and a novel compound of the invention will usually also contain surface-active materials, additional detergency builders which are usually required and other known ingredients of such formulation. Additionally, builders are usually required because the bleach precursor and builder precursor, being part of the same molecule, are present at the same level, but the amount of bleach precursor necessary is usually much lower than the total amount of builder required. In the occasional case, no extra builder will be required.

The surface-active material may be naturally derived, such as soap or may be a synthetic material and may be selected from anionic, nonionic, amphoteric, zwitterionic and cationic actives as well as mixtures thereof. Many suitable actives are commercially available and are fully described in the literature, for example, in "Surface Active Agents and Detergents", Volumes I and II, by Schwartz, Perry and Berch. The total level of the surface-active material may range up to 50% by weight, preferably being from about 1% to 40% by weight of the composition, most preferably 4 to 25%.

Synthetic anionic surface-actives are usually water-soluble alkali metal salts of organic sulfates and sulfonates having alkyl radicals containing from about 8 to about 22 carbon atoms, the term alkyl being used to include the alkyl portion of higher aryl radicals.

Examples of suitable synthetic anionic detergent compounds are sodium and ammonium alkyl sulfates, especially those obtained by sulfating higher ($C_8$–$C_{18}$) benzene sulfonates, particularly sodium linear secondary alkyl ($C_{10}$–$C_{15}$) benzene sulphonates; sodium alkyl glyceryl ether sulfates, especially those ethers of the higher alcohols derived from tallow or coconut oil and synthetic alcohols derived from petroleum; sodium coconut oil fatty acid monoglyceride sulfates and sulfonates; sodium and ammonium salts of sulfuric acid esters of higher ($C_9$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolyzing with a base to produce a random sulfonate; sodium and ammonium $C_7$–$C_{12}$ dialkyl sulfosuccinates; and olefin sulfonates, which term is used to describe the material made by reacting olefins, particularly $C_{10}$–$C_{20}$ alpha olefins, with $SO_3$ and then neutralizing and hydrolyzing the reaction product. The preferred anionic detergent compounds are sodium ($C_{11}$–$C_{15}$) alkylbenzene sulfonates, sodium ($C_{16}$–$C_{18}$) alkyl sulfates and sodium ($C_{16}$–$C_{18}$) alkyl ether sulfates.

Examples of suitable nonionic surface-active compounds which may be used, preferably together with the anionic surface-active compounds, include in particular the reaction products of alkylene oxides, usually ethylene oxide with alkyl ($C_6$–$C_{22}$) phenols, generally 5–25 EO, i.e. 5–25 units of ethylene oxides per molecule: the condensation products of aliphatic ($C_8$–$C_{18}$) primary or secondary linear or branched alcohols with ethylene oxide, generally 6–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

As stated above, soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 15%, are used to give a beneficial effect on detergency. This is particularly valuable in compositions used in hard water when the soap acts as a supplementary builder.

The detergent compositions of the invention will normally also contain an additional detergency builder, as mentioned above. Builder materials may be selected from (1) calcium sequestrant materials, (2) precipitation materials, (3) calcium ion-exchange materials and (4) mixtures thereof but must be compatible with the builder portion of the novel molecule.

Examples of sequestrant builder materials include alkali metal polyphosphates, such as sodium tripolyphosphate although phosphate builders are not preferred; nitrilotriacetic acid and its water-soluble salts; the alkali metal salts of carboxymethyloxy succinic acid, ethylene diamine teraacetic acid, oxydisuccinic acid, mellitic acid, benzene polycarboxylic acids, citric acid; and polyacetalcarboxylates as disclosed in U.S. Pat. Nos. 4,144,226 and 4,146,495.

Examples of precipitating builder materials include sodium orthophosphate, although this is not preferred, sodium carbonate and long-chained fatty acid soaps.

Examples of calcium ion-exchange builder materials include the various types of water-insoluble crystalline or amorphous aluminosilicates, of which zeolites are the best known representatives.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxylmethylmalonate, carboxymethyloxysuccinate and the water-insoluble crystalline or amorphous aluminosilicate builder materials, or mixtures thereof. Preferably, however, the builders are non phosphate containing materials.

These builder materials may be present at a level of, for example, from 5 to 80% by weight, preferably from 10 to 60% by weight.

When the peroxygen compound and bleach precursor are dispersed in water, a peroxy acid (II) is generated:

$$R-(O)_x-\overset{\overset{O}{\|}}{C}-OOH \qquad II$$

where R and x have the values previously assigned.

This peroxy acid should deliver from about 0.1 to about 50 ppm active oxygen per liter of water; preferably oxygen delivery should range from 2 to 15 ppm. Surfactant should be present in the wash water from about 0.05 to 1.0 grams per liter, preferably from 0.15 to 0.20 grams per liter. When present, the builder amount will range from about 0.1 to 3.0 grams per liter. The builder aspect of the invention will, thus, be directly related to the amount of bleach used and so auxiliary builders will usually be necessary.

Apart from the components already mentioned, the detergent compositions of the invention can contain any of the conventional additives in the amounts in which such materials are normally employed in fabric washing detergent compositions. Examples of these additives include lather boosters such as alkanolamides, particularly the monoethanolamides derived from palmkernel fatty acids and coconut fatty acids, lather depressants such as alkyl phosphates and silicones, anti-redeposition agents such as sodium carboxymethylcellulose and alkyl or substituted alkyl cellulose ethers, other stabilizers such as ethylene diamine teraacetic acid, fabric softening agents, inorganic salts such as sodium sulphate, and, usually present in very small amounts, fluorescent agents, perfumes, enzymes such as proteases, cellulses, lipases and amylases, germicides and colorants.

The bleach/builder precursors and their peroxycarbonic acid derivatives described herein are useful in a variety of cleaning products. These include laundry detergents, laundry bleaches, hard surface cleaners, toilet bowl cleaners, automatic dishwashing compositions and even denture cleaners. Precursors of the present invention can be introduced in a variety of product forms including powders, on sheets or other substrates, in pouches, in tablets or in non-aqueous liquids such as liquid nonionic detergents.

A typical detergent formulation of the invention containing the novel Builder/Bleach precursor molecules is as follows:

| Component | Percentage |
|---|---|
| Surfactant | 0-50% |
| Builder/Bleach precursor | 1-10% |
| Auxiliary Bleach precursors | 0-10% |
| Auxiliary Builder | 0-40% |
| Perforate/Percarbonate | 2-25% |
| Silicate | 5-15% |
| Enzyme | 0-5% |
| Filler | 0-40% |
| Adjuncts, Perfumes | 0-5% |
| Fluorescent Whitener, Anti Redeposition Agent and the like. | |
| Water | to 100% |

The following examples will more fully illustrate the embodiments of this invention. All parts, percentages and proportions referred to herein and in the appended claims are by weight unless otherwise indicated.

EXAMPLE 1

Preparation of Disodium, 4-Benzoyloxy-2,6-Pyridinedicarboxylic Acid (BPD)

A 100 ml four-necked round bottom flask equipped with a mechanical stirrer, condenser, additional funnel and thermometer was charged with 3.28 g (0.0819 moles) of sodium hydroxide pellets in 40 ml of distilled water. The alkaline mixture was cooled with an ice bath to 5° C. and then 5.00 g (0.0273 moles) of 1,4-dihydro-4-oxo-2,6-pyridinedicarboxylic acid (chelidamic acid) was introduced over 10 minutes. The color of the reaction was light tan. To the reaction mixture was added 3.84 g (0.0273 moles) of benzoyl chloride over 20 minutes at 5°-10° C. A precipitate immediately formed and the rate of agitation was increased. The temperature of the reaction mixture was held at 10°-15° C. for 30 minutes with vigorous stirring. The ice bath was removed and the temperature of the reaction mixture was allowed to increase to 23° C. At this point the crude product was collected on to a Buchner funnel and washed twice with 30 ml of cold distilled water.

NMR (DMSO-d6, TMS external reference): 7.4-8.3 (m, 7H).

IR (nujol mull): 1730 cm$^{-1}$ (carbonyl ester).

EXAMPLE 2

Preparation of Disodium, 4-(3-Chloromethyl)benzoyloxy-2,6-Pyridinedicarboxylic Acid (CBPD)

A 50 ml four-necked round bottom flask equipped with a mechanical stirrer, additional funnel, condenser and thermometer was charged with 1.97 (0.0492 moles) of sodium hydroxide pellets in 13 ml of distilled water. The alkaline mixture was colled in an ice bath to 5° C. and then 3.00 g (0.0164 moles) of chelidamic acid was introduced over 10 minutes. The color of the solution turned tan. To the reaction mixture was added 3.20 g (0.0164 moles) of 3-(chloromethyl)benzoyl chloride dropwise over 25 minutes. The rate of agitation was increased and a precipitate formed after half of the acid chloride was introduced. The temperature of the reaction was held at 10°-15° C. for 30 minutes with vigorous stirring. The ice bath was removed and the temperature of the reaction was allowed to reach room temperature. The material in the flask was stirred for two hours and collected onto a Buchner funnel. The precipitate was washed with 15 ml of cold distilled water.

NMR (DMSO-d6, TMS external reference): 4.90 (s, 2H), 7.4–8.3 (m, 6H).

IR (nujol mull): 1730 cm$^{-1}$ (carbonyl ester).

EXAMPLE 3

Preparation of Disodium, 4-Choline Carbonate-2,6-Pyridinedicarboxylic Acid (CCPD)

A 50 ml four-necked round bottom flask equipped with a mechanical stirrer, condenser, thermometer and pH meter was charged with 2.00 g (0.0492 moles) of sodium hydroxide pellets in 13 ml of distilled water. After the sodium hydroxide was dissolved, 3.16 g (0.0164 moles) of chelidamic acid was added and stirred rapidly for 15 minutes. A pH of 11.00 was obtained. The reaction mixture was cooled in an ice bath to 5° C. and then 3.31 g (0.0164 moles) of choline chloroformate was rapidly added. A precipitate immediately formed and the rate of agitation increased. The temperature of the reaction was held for 30 minutes at 5° C. The crude product was filtered and slurried with 50 ml of ethanol. The purified product was filtered and washed three times with 35 ml of ethanol.

NMR (D$_2$O, TMS external standard): 3.3 (s, 9H), 3.9 (m, 2H), 4.9 (m, 2H) and 8.0 (s, 2H).

EXAMPLE 4

Peracid Generation From Precursors

The precursors described herein can be used to generate peroxycarbonic acid bleaches in basic aqueous solution containing a source of hydrogen peroxide and, optimally, may contain typical detergent ingredients. Peroxycarbonic acid generation is demonstrated by adding a premeasured sample of precursor to 500 ml aqueous buffer solution at the desired pH, heated to 40° in a thermojacketed beaker, and containing the approximate level of hydrogen peroxide (added as either 30% hydrogen peroxide or sodium perborate monohydrate). The hydrogen peroxide source is added just prior to addition of the precursor. Ten milliliter aliquots of solution are withdrawn from the beaker at regular intervals and are added to a 250 ml titration flask containing crushed ice (150 g), glacial acetic acid (30 ml) and 4% aqueous potassium iodide (5 ml). After development for ten minutes with occasional agitation, the iodine produced is titrated with standard sodium thiosulfate solution. Time zero is taken as the point of introduction of precursor into the peroxyide solution. Precursor perhydrolysis experiments are generally carried out for a maximum of 15 minutes.

Since hydrogen peroxide itself contributes to the total active oxygen in these titrations, controls or "blanks" are obtained by carrying out a perhydrolysis experiment in the absence of precursor. These hydrogen peroxide blanks are subtracted from the total active oxygen titration in the presence of bleach precursor to give the level of active oxygen produced by precursor perhydrolysis.

Peroxycarbonic acid generation is determined at pH 8, 9, and 10. Borax buffer is used for experiments at pH 9 and 10 while phosphate buffer is employed for experiments carried out at pH 8. Adjustment of the buffer systems at 40° C. to the exact pH is carried out with 1M hydrochloric acid or sodium hydroxide solution.

Table I lists the peroxycarbonic acid yields as a percent of theoretical from BPD.

TABLE 1

| | Perhydrolysis yields from BPD | | |
|---|---|---|---|
| pH | 1 minute | 8 minutes | 15 minutes |
| 10 | 91.35% | 17.63% | 0% |

Conditions: 40° C. [BPD] = 6.24 × 10$^{-4}$ M
[H$_2$O$_2$] = 6.24 × 10$^{-3}$ M

Determination of Stain Bleaching

The stain bleaching ability of peroxycarbonic acids generated from the synthesized precursors is demonstrated on a tea stain. Typically, cotton test pieces (4 in. × 4 in.) stained with the tea are washed in a Terg-O-Tometer in 1 l. of aqueous solution containing a given level of bleach precursor, hydrogen peroxide, buffer, and surfactant (generally sodium dodecylbenzenesulfonate).

Washes are carried out at 40° C. for 15 minutes. Stain bleaching is measured reflectrometrically using a Colorgard System/05 Reflectometer. Bleaching is indicated by an increase in reflectance, reported as ΔR. In general a ΔR of one unit is perceivable in a paired comparison while ΔR of two units is perceivable monadically. In reporting the reflectance change, the change in reflectance caused by general detergency and bleaching by the excess hydrogen peroxide has been accounted for. Thus ΔR can actually be expressed as: ΔR=(the value of the Reflectance of stained fabric washed with precursor, H$_2$O$_2$ and detergent minus the value of the Reflectance of stained fabric before washing) minus (the value of the Reflectance of stained fabric washed with H$_2$O$_2$ and detergent alone minus the value of the Reflectance of stained fabric before washing).

TABLE 2

| Bleaching Performance | |
|---|---|
| Percursor | Δ R |
| (BPD) | >6.0 |
| (CBPD) | >6.0 |
| (CCPD) | >15.0 |

Conditions: 40° C. BC-1 cloth, pH = 9.0–9.5, [precursor] = 6.2 × 10$^{-4}$ M, [H$_2$O$_2$] = 6.25 × 10$^{-3}$ M.

The formulation of the detergent base used for the bleaching test is as follows:

| | |
|---|---|
| Sodium Sulfate | 28% |

| | |
|---|---|
| Pentasodium tripolyphosphate | 30% |
| Sodium Alkylbenzene Sulfonate | 15% |
| Sodium Silicate 2.4 to 1 ratio | 11% |
| Water | 9% |
| Sodium Carbonate | 5% |
| Miscellaneous | |
| Sodium Carboxymethylcellulose, | 2% |
| Perfume, | |
| Fluorescent Whitening Agent, | |
| Colorant | |

DETERMINATION OF CALCIUM BINDING

Calcium binding data was obtained at a pH of 10 by titrating 100 ml of 0.05 g/l precursor solution at an ionic strength of 0.02–0.03M (NaCl) with a 0.02M $CaCl_2$ solution. A Radiometer calcium ion selective electrode was used to measure free $Ca^{++}$ ion concentration of the solutions. Data was corrected for dilution during each titration.

Results of tests run on the compounds prepared as in Examples 1, 2 and 3 are reported in Table 3:

TABLE 3

| Binding Constants | |
|---|---|
| | Log $K_{Ca}$ |
| Chelidamic Acid | 5.70 |
| Sodium Tripolyphosphate | 5.85 |

This invention has been described with respect to certain preferred embodiments, and various modifications and variations in the light thereof will be suggested to persons skilled in the art and are to be included within the spirit and purview of this application and the scope of the appended claims.

What is claimed is:

1. A multifunctional compound of the formula

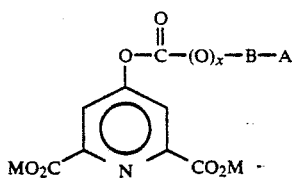

where x may be 0 or 1;
where M is alkali metal or hydrogen;
where B is $(CH_2)_y$ and y is 2–8 or where B is aryl, substituted aryl, or heterocyclic;
where A is R and R may be about $C_{1-14}$ alkyl, aryl, substituted alkyl, or substituted aryl,
or where A is

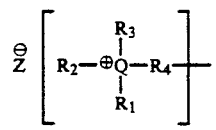

and
$R_1$, $R_2$ and $R_3$ are each independently a radical selected from the group consisting of alkyl, alkenyl, alkynyl, cycloalkyl, cycloalkenyl, alkaryl, aryl, hydroxyalkyl, polyoxyalkylene, and $R_4(O)_m$-$C(O)_nR_1$;

or two or more of $R_1$, $R_2$ and $R_3$ together form an alkyl substituted or unsubstituted nitrogen-containing heterocyclic ring system;
or at least one of $R_1$, $R_2$ and $R_3$ is attached to $R_4$ to form an alkyl substituted or unsubstituted nitrogen-containing heterocyclic ring system; and
$R_4$ is selected from a bridging group consisting of alkylene, cycloalkylene, alkylenephenylene, phenylene, arylene, and polyalkoxylene, and wherein the bridging group can be unsubstituted or substituted with $C_1$–$C_{20}$ atoms selected from alkyl, alkenyl, benzyl, phenyl and aryl radicals;
$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;
Q is nitrogen or phosphorous;
m and n are the same or different and either 0 or 1 or where B and A together are 2,4 pyridine dicarboxylic acid sodium salt.

2. A compound as defined in claim 1 having the formula

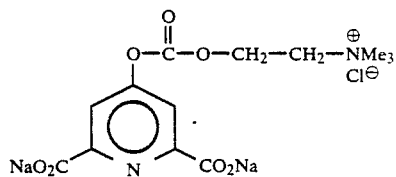

4-cholylcarbonate-2,6-pyridinedicarboxylic acid disodium salt.

3. A compound as defined in claim 1 having the formula

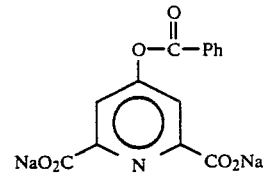

disodium 4-benzyoloxy-2,6-pyridinedicarboxylate.

4. A bleaching-detergent composition comprising:
(i) from 1 to 60% of a peroxygen compound capable of yielding hydrogen peroxide in an aqueous solution;
(ii) from 0.1 to 40% of a compound having the formula:

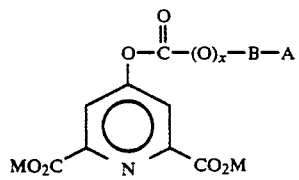

where x may be 0 or 1;
where M is alkali metal or hydrogen;
where B is $(CH_2)_y$ and y is 2–8 or where B is aryl, substituted aryl, or heterocyclic;
where A is R and R may be about $C_{1-14}$ alkyl, aryl, substituted alkyl, substituted aryl, or quaternary ammonium carboxylic esters;

or where A is

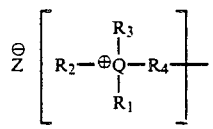

and $R_1$, $R_2$ and $R_3$ are each independently a radical selected from the group consisting of alkyl, alkenyl, alkynyl, cycloalkyl, cycloalkenyl, alkaryl, aryl, hydroxyalkyl, polyoxyalkylene, and $R_4(O)_mC(O)_nR_1$;

or two or more of $R_1$, $R_2$ and $R_3$ together form an alkyl substituted or unsubstituted nitrogen-containing heterocyclic ring system;

or at least one of $R_1$, $R_2$ and $R_3$ is attached to $R_4$ to form an alkyl substituted or unsubstituted nitrogen-containing heterocyclic ring system; and $R_4$ is selected from a bridging group consisting of alkylene, cycloalkylene, alkylenephenylene, phenylene, arylene, and polyalkoxylene, and wherein the bridging group can be unsubstituted or substituted with $C_1$-$C_{20}$ atoms selected from alkyl, alkenyl, benzyl, phenyl and aryl radicals;

$Z^{31}$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorous;

m and n are the same or different and either 0 or 1;

(iii) from 0 to 50% of a surfactant selected from the group consisting of nonionic, anionic, amphoteric and surface active mixtures thereof;

(iv) from 0 to 80% of a detergent builder and (v) 0.2 to 5% of an enzyme.

5. The composition of claim 4 wherein the surfactant ranges from 4 to 50% and the detergent builder ranges from 5 to 70% by weight.

6. A detergent formulation comprising:

| Component | Percentage |
| --- | --- |
| Surfactant | 0-50% |
| Builder/Bleach precursor of claim 1 | 1-10% |
| Auxiliary Builder | 0-40% |
| Auxiliary Bleach precursor | 0-10% |
| Perborate/Percarbonate | 2-25% |
| Silicate | 5-15% |
| Enzyme | 0-5% |
| Filler | 0-40% |
| Adjuncts, including Perfume, Fluorescent Whitener, Anti-Redeposition Agent and the like. | 0-5% |

* * * * *